(12) United States Patent
Wang et al.

(10) Patent No.: US 9,005,986 B2
(45) Date of Patent: Apr. 14, 2015

(54) METHOD FOR RAPIDLY MEASURING MELATONIN ADULTERATION OF CHINESE PATENT MEDICINE OR HEALTHCARE FOOD

(75) Inventors: Tiejie Wang, Shenzhen (CN); Yi Lu, Shenzhen (CN); Lihe Xiao, Shenzhen (CN); Xiaoying Guan, Shenzhen (CN); Dongqi Han, Shenzhen (CN); Guo Yin, Shenzhen (CN); Jue Wang, Shenzhen (CN); Xueqing Li, Shenzhen (CN); Yan Yan, Shenzhen (CN)

(73) Assignee: Shenzhen Institute For Drug Control, Shenzhen (CN)

( * ) Notice: Subject to any disclaimer, the term of this patent is extended or adjusted under 35 U.S.C. 154(b) by 0 days.

(21) Appl. No.: 14/346,532

(22) PCT Filed: Jul. 2, 2012

(86) PCT No.: PCT/CN2012/078069
§ 371 (c)(1),
(2), (4) Date: Mar. 21, 2014

(87) PCT Pub. No.: WO2013/056572
PCT Pub. Date: Apr. 25, 2013

(65) Prior Publication Data
US 2014/0220698 A1     Aug. 7, 2014

(30) Foreign Application Priority Data

Oct. 18, 2011   (CN) .......................... 2011 1 0316788

(51) Int. Cl.
*G01N 33/94* (2006.01)
*G01N 21/78* (2006.01)
*G01N 33/74* (2006.01)
*G01N 33/52* (2006.01)
*G01N 33/00* (2006.01)

(52) U.S. Cl.
CPC ....... *G01N 33/94* (2013.01); *Y10T 436/145555* (2015.01); *G01N 21/78* (2013.01); *G01N 33/74* (2013.01); *G01N 33/52* (2013.01)

(58) Field of Classification Search
CPC ....... G01N 33/94; G01N 33/15; G01N 24/08; G01N 33/52; G01N 33/74; Y10T 43/145555
USPC ................. 436/96, 86, 173; 435/90; 324/309
See application file for complete search history.

(56) References Cited

U.S. PATENT DOCUMENTS 6,806,090 B1 *   10/2004   Hylands et al. ................. 436/86

OTHER PUBLICATIONS http://www.google.com/patents/CN1742588A?cl=en.*

* cited by examiner

*Primary Examiner* — Rebecca M Fritchman
(74) *Attorney, Agent, or Firm* — Shimokaji IP

(57) ABSTRACT

A method for rapidly measuring melatonin adulteration of Chinese patent medicines and healthcare foods comprises: (1) extracting melatonin added to a Chinese patent medicine or healthcare food by using ethyl acetate; and (2) adding p-dimethylaminocinnamaldehyde to the extracted solution, and observing color. The method is rapid, simple and convenient, has strong specificity, high accuracy, reaction sensitivity, and a wide application range, and is applicable to on-site detection of melatonin adulteration of a Chinese patent medicine or healthcare food.

5 Claims, No Drawings

METHOD FOR RAPIDLY MEASURING MELATONIN ADULTERATION OF CHINESE PATENT MEDICINE OR HEALTHCARE FOOD

PRIORITY INFORMATION

The present application claims priority to Chinese Application No. 201110316788.3, entitled Method for Rapidly Measuring Melatonin Adulteration of Chinese Patent Medicine or Healthcare Food, filed on Oct. 18, 2011, the entire contents of which are hereby incorporated by reference.

FIELD OF THE INVENTION

The present invention relates to a method for measuring melatonin components, specifically for detecting whether there is melatonin added to Chinese patent medicine or healthcare food, especially to sedative hypnotic Chinese patent medicine or healthcare food.

BACKGROUND OF THE INVENTION

Currently, there are many commercially available Chinese patent medicines or healthcare foods that promise to solve the problem of insomnia, which is also declared to be composed of pure plant or pure traditional Chinese medicine, do not contain Western medicine used to treat sleep problems or hormones.

Melatonin, also known chemically as N-acetyl-5-methoxytryptamine, is a kind of indoleamine hormone secreted by the pineal gland located in the human brain. Known as the "hormone of darkness", melatonin secretion decreases with increasing intensity of light. Melatonin is mainly used to regulate sleep-wake cycle and physiological circadian rhythms. Melatonin also has anti-aging properties.

Melatonin is a kind of endogenous hormone. Some studies have shown that heavy use of melatonin may cause breathing problems and hangover effect. Meanwhile, melatonin may impact on some sedative hypnotic drug's efficacy, such as clonazepam. In Europe, dosage interval, target population and dosage are all strictly restricted. In the US, melatonin can be sold in the form of dietary supplements. The label must include content and dosage instructions. In China, melatonin is used as healthcare food. There are clear legal provisions: daily dosage restriction of melatonin is 1-3 mg; no ingredients can be added except vitamin B6; the section of "warning" should tell the people who engage in mechanical work or dangerous operation not to use before they work/while they are working; meanwhile, it should also tell the people having autoimmune disease (rheumatism, etc.) or hyperthyroidism disease to use with caution. Thus, melatonin should be consumed according to doctor's advice. The dosage must be confirmed. Melatonin should be used with more caution in children. However, due to good sedative hypnotic effect of melatonin and complex ingredients of Chinese patent medicine and healthcare food, some unscrupulous people add melatonin to sedative hypnotic Chinese patent medicine or healthcare food illegally. They hype the effect of the products in order to drive up prices. It makes users not clearly aware of their dosage, thus causing adverse consequences and harm to the people's health. Especially in some rural area and underdeveloped small cities, lack of necessary testing equipment and weak technical regulation has created opportunities for criminals to employ trickery, resulting in a large number of counterfeit or substandard drugs, causing confusion in the market of traditional Chinese medicine and healthcare food.

The existing methods for detecting whether there is melatonin added to sedative hypnotic Chinese patent medicine or healthcare food mainly include the following four methods:

1. Thin Layer Chromatography (TLC)

The component to be tested is extracted from samples with methanol. A small spot of test solution is applied to a silica gel plate, as well as reference solution. Developing agent is used to develop the plate. Then the plate is taken out, dried, and inspected under ultraviolet lamp at 254 nm. With the help of developing agent, different substances appear at different TLC plate position in the form of spot due to the differences in migration rates. The presence of target components in the samples can be determined by the experimental results that the spot of test sample appears at the same position as the reference. If spot appears on TLC chromatogram of test solution is at the same position as melatonin reference solution, it may indicate the presence of melatonin in the test sample.

Advantage of TLC is free of expensive analytical instrument. Disadvantages are: (1) Low in resolution; traditional Chinese medicine are complex, there are a lot of interference. Some coexisting components can be easily mistaken for melatonin If some coexisting components are in a large amount and chromatographic shift value is close to that of the component to be tested, the detection of target components may be interfered. (2) It takes long time to develop and dry, which fails to meet the requirement of rapid measurement. (3) TLC plate needs to be dried and stored in dry place. Environment temperature and humidity have a great effect on separation. (4) Require fixed location. Not suitable for mobile on-site detection. (5) Require tester with rich experience 2. High Performance Liquid Chromatography (HPLC)

HPLC is commonly used modern analytical method. Under the same chromatographic conditions, different materials have different retention time. Under the same chromatographic conditions, melatonin reference solution and test solution extracted from the sample are injected separately. According to the retention time of chromatographic peak, it can be determined whether the test sample contains melatonin components.

Advantages of HPLC chromatography is high efficiency and high sensitivity. Disadvantages are: (1) The equipment is expensive; it takes long time for pretreatment of sample; the column is vulnerable to be polluted; high cost; (2) It is easy to make a mistake in judgment when the peak retention time of some coexisting components is close to that of melatonin; (3) Instrument has high requirements to the environment, a fixed location is required; not suitable for mobile on-site detection.

3. High Performance Liquid Chromatography—Mass Spectrography (HPLC-MS)

HPLC-MS, using HPLC as separator, mass spectrography as analyzer, is suitable to analyze complex composition, even in the case of serious interference. This analytical method can improve the reliability of the test results.

HPLC-MS is an analytical method, costing more and being more complex than HPLC. Instrument has higher requirements to the environment. Instrument needs to be fixed, and is not suitable for mobile on-site detection. These detections can only be performed in a few laboratories, so it is difficult to promote.

In the field of Chinese patent medicine and healthcare food, the method for rapidly screening melatonin by physical and chemical reaction has not been reported yet. For drugstore and grassroots drug test department, it is very necessary to develop a method for rapidly screening melatonin adulteration of Chinese patent medicine or healthcare food. It will help on-site detection and provide evidence timely for regulation of Chinese patent medicine or healthcare food. It is useful to combat counterfeiting and protect the medication safety of the people.

SUMMARY OF THE INVENTION

The object of the present invention is to provide a low-cost method for rapidly measuring melatonin. The method overcomes deficiencies of the current measurement technique. There is no need to use expensive analytical instrument. The method has strong specificity, high accuracy, reaction sensitivity, and is applicable to on-site detection of melatonin adulteration of Chinese patent medicine or healthcare food.

Another object of the present invention is to provide use of the above method in preparing melatonin test kit.

Yet another object of the present invention is to provide use of the above method in screening melatonin adulteration of Chinese patent medicine or healthcare food.

The method for rapidly measuring melatonin adulteration of Chinese patent medicine or healthcare food, comprising the following steps in sequence:

(1) extracting melatonin from Chinese patent medicine or healthcare food with ethyl acetate;

(2) adding p-dimethylaminocinnamaldehyde to extracted solution as color developing agent.

Melatonin, also known chemically as N-acetyl-5-methoxytryptamine, is a kind of indoleamine hormone. Our studies show that melatonin solution becomes blue-green in color after adding hydrochloric acid ethanol solution of p-dimethylaminocinnamaldehyde.

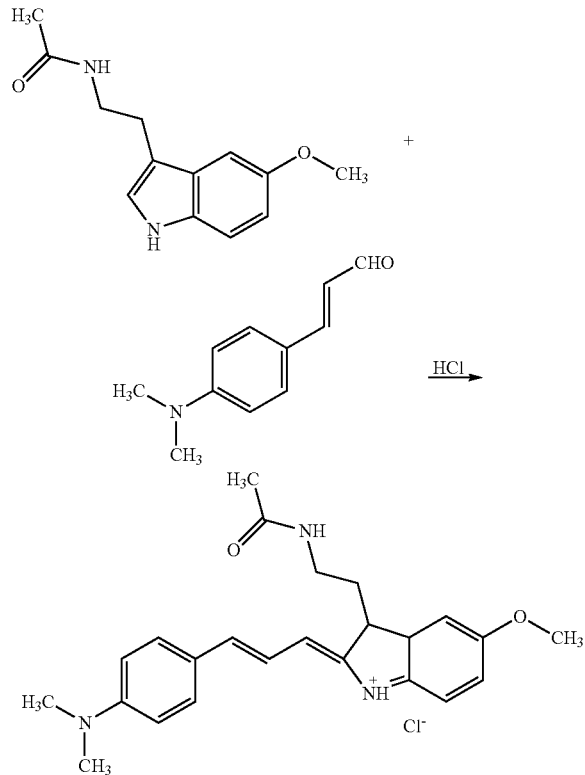

The technical solution is as follows:

1. Solid Chinese patent medicine or healthcare food is grinded, followed by addition of 1-3 mL of ethyl acetate. After shaking for 1 min, the mixture obtained from the previous step is filtrated to get test liquid; or 1-3 mL of ethyl acetate is added to liquid Chinese patent medicine or healthcare food. After shaking for 1 min and standing, then filtrate the ethyl acetate phase to get test liquid.

In relation to most commercially available Chinese patent medicine and healthcare food, recommended amount of samples are as follows:

| | Dosage form | | | | |
|---|---|---|---|---|---|
| | capsule | tablet | pill | granules | oral liquid |
| Amount of samples | 1 capsule | 1 tablet | 1 pill | 1/10 package | 1/5 vial |

2. Preparation of hydrochloric acid ethanol solution of p-dimethylaminocinnamaldehyde: 10 mL of hydrochloric acid ethanol solution having a mass concentration of 40-70% is added to 0.01-0.1 g of p-dimethylaminocinnamaldehyde in order to dissolve p-dimethylaminocinnamaldehyde. Concentration of the hydrochloric acid ethanol solution herein is preferably in the range of 50%-60%. The amount of p-dimethylaminocinnamaldehyde and volume of hydrochloric acid ethanol solution can be adjusted according to the actual situation, but p-dimethylaminocinnamaldehyde and hydrochloric acid ethanol solution are in an amount sufficient to get a hydrochloric acid ethanol solution of p-dimethylaminocinnamaldehyde having a concentration of 1-10 mg/mL.

Ratio of hydrochloric acid to ethanol herein is preferably to be in the range of 1.5:1 to 1:1. More preferably, color developing agent is prepared using hydrochloric acid-ethanol in a ratio of 1:1. The color rendering is excellent when concentration of p-dimethylaminocinnamaldehyde is in the range of 4-6 mg/mL. More preferably, the concentration of hydrochloric acid ethanol solution of p-dimethylaminocinnamaldehyde is 4 mg/mL.

3. 0.5-1 mL of hydrochloric acid ethanol solution of p-dimethylaminocinnamaldehyde is added to the test liquid. If the solution turns blue-green rapidly (exhibiting obvious blue to green in color), the sample contains melatonin; if no obvious blue-green can be observed after 30 s (no obvious blue to green in color), the sample contains no melatonin According to the present invention, melatonin test kit can also be prepared.

According to the present invention, the method can be applied in screening melatonin adulteration of Chinese patent medicine or healthcare food.

Compared to the prior art, the present invention has the following advantages:

(1) Rapid and simple: It takes 1 minute for extraction, 30 seconds for color reaction. The whole process can be completed within 2 minutes. The method is much simpler than liquid chromatography and LC-MS (require at least 2-3 hours). Besides, there is no need to use reference substance.

(2) Strong in specificity and high in accuracy: according to the verified test results, commonly used excipients in tablets, capsules, pills, granules, oral liquid do not interfere with the detection of melatonin.

(3) High in reaction sensitivity: The minimum detection limit of such method is 1/200 of efficient dosage in clinic (average detection limit for the samples is 0.025 mg/ml). Therefore, the method can be used for sensitive detection of melatonin in Chinese patent medicine or healthcare food.

(4) Covers a wide range of application: The method can be applied for liquid sample and solid sample. The method can be applied for both traditional Chinese medicines and healthcare food.

(5) Economical: the material used in the present invention is low in cost, and suitable for popularization and large-scale production.

The method for measuring melatonin of the present invention is also suitable for rapidly measuring melatonin adulteration of other foods having effects on insomnia and sleep.

DETAILED DESCRIPTION OF ILLUSTRATED EMBODIMENTS

While the present invention has been described with reference to particular embodiments, it will be understood that the embodiments are illustrative and that the invention scope is not so limited.

EXAMPLE 1

Healthcare food A purchased from the market (Capsule, dosage according to the label instructions was 1-2 capsules every time. The samples were tested by HPLC, each capsule contains melatonin 1 mg.)

A grain of the containers of such healthcare food A was placed into sample cell. 2 mL of Ethyl acetate was added. After shaking for 1 min and filtrating, the filtrate liquid was used as test liquid. 10 mL of hydrochloric acid ethanol solution having a mass concentration of 50% used as color developing agent was added to 0.04 g of p-dimethylaminocinnamaldehyde to dissolve p-dimethylaminocinnamaldehyde. 1 mL of Hydrochloric acid ethanol solution of p-dimethylaminocinnamaldehyde was added to the test liquid. The solution turned blue-green within 30 s. This indicated that the sample contains melatonin illegally.

EXAMPLE 2

Healthcare food B purchased from the market (Capsule, dosage according to the label instructions was 1-2 capsules every time. The samples were tested by HPLC, each capsule contains melatonin 0.9 mg.)

A grain of the containers of such healthcare food B was placed into sample cell. 3 mL of Ethyl acetate was added. After shaking for 1 min and filtrating, the filtrate liquid was used as test liquid. 10 mL of hydrochloric acid ethanol solution having a mass concentration of 60% used as color developing agent was added to 0.08 g of p-dimethylaminocinnamaldehyde to dissolve p-dimethylaminocinnamaldehyde. 0.5 mL of Hydrochloric acid ethanol solution of p-dimethylaminocinnamaldehyde was added to the test liquid. The solution turned blue-green within 30 s. This indicated that the sample contains melatonin illegally.

Example 3

Healthcare food C purchased from the market (Capsule, dosage according to the label instructions was 1-6 capsules every time. The samples were tested by HPLC, each capsule contains melatonin 1 mg.)

A grain of the containers of such healthcare food C was placed into sample cell. 3 mL of Ethyl acetate was added. After shaking for 1 min and filtrating, the filtrate liquid was used as test liquid. 10 mL of hydrochloric acid ethanol solution having a mass concentration of 40% used as color developing agent was added to 0.1 g of p-dimethylaminocinnamaldehyde to dissolve p-dimethylaminocinnamaldehyde. 0.5 mL of Hydrochloric acid ethanol solution of p-dimethylaminocinnamaldehyde was added to the test liquid. The solution turned blue-green within 30 s. This indicated that the sample contains melatonin illegally.

EXAMPLE 4

Healthcare food D purchased from the market (Capsule, dosage according to the label instructions was 2 capsules every time. The samples were tested by HPLC, each capsule contains melatonin 1.8 mg.)

A grain of the containers of such healthcare food D was placed into sample cell. 3 mL of Ethyl acetate was added. After shaking for 1 min and filtrating, the filtrate liquid was used as test liquid. 10 mL of hydrochloric acid ethanol solution having a mass concentration of 40% used as color developing agent was added to 0.01 g of p-dimethylaminocinnamaldehyde to dissolve p-dimethylaminocinnamaldehyde. 0.5 mL of Hydrochloric acid ethanol solution of p-dimethylaminocinnamaldehyde was added to the test liquid. The solution turned blue-green within 30 s. This indicated that the sample contains melatonin illegally.

EXAMPLE 5

Healthcare food E purchased from the market (Capsule, dosage according to the label instructions was 2 capsules every time. The samples were tested by HPLC, each capsule contains melatonin 0.9 mg.)

A grain of the containers of such healthcare food E was placed into sample cell. 1 mL of Ethyl acetate was added. After shaking for 1 min and filtrating, the filtrate liquid was used as test liquid. 10 mL of hydrochloric acid ethanol solution having a mass concentration of 70% used as color developing agent was added to 0.05 g of p-dimethylaminocinnamaldehyde to dissolve p-dimethylaminocinnamaldehyde. 0.6 mL of Hydrochloric acid ethanol solution of p-dimethylaminocinnamaldehyde was added to the test liquid. The solution turned blue-green within 30 s. This indicated that the sample contains melatonin illegally.

EXAMPLE 6

Healthcare food F purchased from the market (Tablet, dosage according to the label instructions was 2 tablets every time. The samples were tested to be melatonin-free by HPLC-MS, for negative control test use.)

A tablet of such healthcare food F was grinded and placed into sample cell. 2 mL of Ethyl acetate was added. After shaking for 1 min and filtrating, the filtrate liquid was used as test liquid. 10 mL of hydrochloric acid ethanol solution having a mass concentration of 50% used as color developing agent was added to 0.04 g of p-dimethylaminocinnamaldehyde to dissolve p-dimethylaminocinnamaldehyde. 1 mL of Hydrochloric acid ethanol solution of p-dimethylaminocinnamaldehyde was added to the test liquid. The color of the solution did not change within 30 s. This indicated that the sample contains no melatonin.

EXAMPLE 7

Chinese patent medicine G purchased from the market (Capsule, dosage according to the label instructions was 4 capsules every time. The samples were tested to be melatonin-free by HPLC-MS, for negative control test use.)

A grain of the containers of such Chinese patent medicine G was placed into sample cell. 3 mL of Ethyl acetate was added. After shaking for 1 min and filtrating, the filtrate liquid was used as test liquid. 10 mL of hydrochloric acid ethanol solution having a mass concentration of 50% used as color developing agent was added to 0.04 g of p-dimethylaminocinnamaldehyde to dissolve p-dimethylaminocinnamaldehyde. 1 mL of Hydrochloric acid ethanol solution of p-dimethylaminocinnamaldehyde was added to the test liquid. The color of the solution did not change within 30 s. This indicated that the sample contains no melatonin

EXAMPLE 8

Chinese patent medicine H purchased from the market (Pill, dosage according to the label instructions was about 28 pills every time. The samples were tested to be melatonin-free by HPLC-MS, for negative control test use.)

A pill of such Chinese patent medicine H was grinded and placed into sample cell. 1 mL of Ethyl acetate was added. After shaking for 1 min and filtrating, the filtrate liquid was used as test liquid. 10 mL of hydrochloric acid ethanol solution having a mass concentration of 50% used as color developing agent was added to 0.04 g of p-dimethylaminocinnamaldehyde to dissolve p-dimethylaminocinnamaldehyde. 1 mL of Hydrochloric acid ethanol solution of p-dimethylaminocinnamaldehyde was added to the test liquid. The color of the solution did not change within 30 s. This indicated that the sample contains no melatonin.

EXAMPLE 9

Chinese patent medicine I purchased from the market (Oral liquid, dosage according to the label instructions was 10-20 mL every time. The samples were tested to be melatonin-free by HPLC-MS, for negative control test use.)

2 mL of such Chinese patent medicine I was placed into sample cell. 2 mL of Ethyl acetate was added. After shaking for 1 min and standing, ethyl acetate phase was taken and filtrated, the filtrate liquid was used as test liquid. 10 mL of hydrochloric acid ethanol solution having a mass concentration of 50% used as color developing agent was added to 0.04 g of p-dimethylaminocinnamaldehyde to dissolve p-dimethylaminocinnamaldehyde. 1 mL of Hydrochloric acid ethanol solution of p-dimethylaminocinnamaldehyde was added to the test liquid. The color of the solution did not change within 30 s. This indicated that the sample contains no melatonin.

EXAMPLE 10

Chinese patent medicine J purchased from the market (Granules, dosage according to the label instructions was 5 g every time. The samples were tested to be melatonin-free by HPLC-MS, for negative control test use.)

0.5 g of such Chinese patent medicine J was grinded and placed into sample cell. 3 mL of Ethyl acetate was added. After shaking for 1 min and filtrating, the filtrate liquid was used as test liquid. 10 mL of hydrochloric acid ethanol solution having a mass concentration of 50% used as color developing agent was added to 0.04 g of p-dimethylaminocinnamaldehyde to dissolve p-dimethylaminocinnamaldehyde. 1 mL of Hydrochloric acid ethanol solution of p-dimethylaminocinnamaldehyde was added to the test liquid. The color of the solution did not change within 30 s. This indicated that the sample contains no melatonin.

Rapid Screening Method Assessment

Tests were carried out on 80 samples, which consist of Chinese patent medicine having sedative and tranquilization effect, healthcare food having the function of improving sleep and healthy products having the same function according to the label instructions. The test results were verified by related verification method and shown in Table. 1:

TABLE 1

| Rapid screening result | Verified test results | | |
|---|---|---|---|
| | Final result | | |
| | Melatonin-added | Melatonin-free | Total |
| positive | True positive A (25) | False positive B (1) | 26 |
| negative | False negative C (0) | True negative D (54) | 54 |
| Total | 25 | 55 | 80 |

As requested by Guangdong Institute for Drug Control, according to the "Guidelines and Technical Requirements to Method for Rapidly Screening Chemical Components Adulteration of Chinese Patent Medicine or Healthcare Food (for trial implementation)", summary table of the rapid screening method is shown in Table. 2:

TABLE 2

| summary table of the Rapid screening method | |
|---|---|
| Sample source | 80 samples collected from market (purchased from the market, sampling from circulation) there are 25 positive samples |
| Dosage form | Capsule, tablet, granules, pill, oral liquid |
| Minimum detection limit | The minimum detection limit of such method is one twentieth of efficient dosage in clinic. |
| Sensitivity | 100% |
| Specificity | 98.1% |
| Missing rate | 0% |
| False rate | 1.9% |
| Accuracy | 98.7% |
| Youden's index | 98.7% |
| Testing time | Less than 2 minutes per sample |
| Professional skill requirements | Simply trained |
| Operating conditions | Operate on site |

It can be seen that the method can be used to for rapidly screening melatonin adulteration of healthy products. The method is rapid, simple and convenient, has strong specificity, high accuracy, reaction sensitivity, and a wide application range, and is applicable to on-site detection of melatonin as required by grass root inspection.

What is claimed is:

1. A method for rapidly measuring melatonin adulteration of Chinese patent medicine or healthcare food, comprising the following steps in sequence:
    (1) obtaining a sample of Chinese patent medicine/healthcare food suspected of having been adulterated with melatonin;
    (2) adding ethyl acetate to the sample to form a test liquid;
    (3) adding p-dimethylaminocinnamaldehyde and a hydrochloric acid ethanol solution to the test liquid;
    (4) and observing if there is a change in color in the test liquid that the Chinese patent medicine or healthcare food has been adulterated with melatonin.

2. The method according to claim 1, wherein mass concentration of said hydrochloric acid ethanol solution is in the range of 40%-70%.

3. The method according to claim 2, wherein concentration of said p-dimethylaminocinnamaldehyde in the hydrochloric acid ethanol solution is in the range of 1-10 mg/mL.

4. The method according to claim 1, comprising the following steps in sequence:

(1) grinding Chinese patent medicine or healthcare food, adding ethyl acetate and shaking, filtrating, taking filtrate liquid as the test liquid;
(2) taking 0.01-0.1 g of p-dimethylaminocinnamaldehyde, adding 10 mL of a hydrochloric acid ethanol solution having a mass concentration of 40%-70% used as color developing agent to dissolve p-dimethylaminocinnamaldehyde;
(3) adding a hydrochloric acid ethanol solution of p-dimethylaminocinnamaldehyde to said test liquid, and observing if there is a change in color that the Chinese patent medicine or healthcare food has been adulterated with melatonin.

5. The method according to claim 1, wherein concentration of said p-dimethylaminocinnamaldehyde in the hydrochloric acid ethanol solution is in the range of 1-10 mg/mL.

\* \* \* \* \*